(12) United States Patent
Bozdag

(10) Patent No.: US 8,430,814 B2
(45) Date of Patent: Apr. 30, 2013

(54) ANOSCOPE

(76) Inventor: Ali Dogan Bozdag, Izmir (TR)

( * ) Notice: Subject to any disclaimer, the term of this patent is extended or adjusted under 35 U.S.C. 154(b) by 597 days.

(21) Appl. No.: 12/159,780

(22) PCT Filed: Mar. 6, 2007

(86) PCT No.: PCT/IB2007/050730
§ 371 (c)(1),
(2), (4) Date: Jun. 30, 2008

(87) PCT Pub. No.: WO2007/116327
PCT Pub. Date: Oct. 18, 2007

(65) Prior Publication Data
US 2009/0005647 A1 Jan. 1, 2009

(30) Foreign Application Priority Data
Apr. 11, 2006 (TR) .................................. 2006 01741

(51) Int. Cl.
*A61B 1/32* (2006.01)

(52) U.S. Cl.
USPC ........... 600/245; 600/200; 600/210; 600/197; 600/234; 600/117

(58) Field of Classification Search .......... 600/184–249; 607/138
See application file for complete search history.

(56) References Cited

U.S. PATENT DOCUMENTS

| 457,787 A * | 8/1891 | Leisenring ..................... 600/184 |
| 4,819,620 A | 4/1989 | Okutsu |
| 4,834,067 A * | 5/1989 | Block ........................... 600/184 |
| 2003/0130559 A1* | 7/2003 | Morin et al. ................... 600/104 |
| 2003/0163026 A1* | 8/2003 | Fontana ......................... 600/135 |
| 2006/0009797 A1 | 1/2006 | Armstrong |
| 2006/0036129 A1 | 2/2006 | Sias |

FOREIGN PATENT DOCUMENTS

| WO | 2004/021874 A | 3/2004 |
| WO | WO 2004/021874 A1 * | 3/2004 |

* cited by examiner

*Primary Examiner* — Kevin T Truong
*Assistant Examiner* — Samuel Hanna
(74) *Attorney, Agent, or Firm* — Venable, Campillo, Logan & Meaney PC

(57) ABSTRACT

This invention relates to an anoscope (1) that comprises a back piece (3) to stand on; a handle (6) with a longitudinal axis that faces the front piece (2) of the anoscope (1), particularly the sliding lid (5) and the window (11) when the lid (5) is opened; a broadly piece (7) that is located at the junction of the handle (6) and the front piece (2) and that sits on the front piece (2); a socket (8) on the surface of the atrium (23) of the broadly piece (7); a cylindrical extension (17) inside the broadly piece (7); a sliding lid (5) located on the front piece (2) that can either be separated totally from the front piece (2) or can form a window (11) that opens to the desired extent; a protrusion (12) located at the inner surface of the sliding lid (5) that facilitates the lid (5) being handled and pulled; a tongue (9) distal to the front piece (2) that sits on the socket (8) and manages locking and unlocking processes of the front piece (2) and the back piece (3); and a pillar (21) and a console (22) located on both sides of the tongue (9) that are used to unlock and remove the front piece (2).

8 Claims, 6 Drawing Sheets

ANOSCOPE

FIELD OF THE INVENTION

This invention relates to anoscope which is used in hemorrhoidal surgery.

BACKGROUND OF THE INVENTION

The present state of the art involves anoscopes that are used in hemorrhoidal surgery. Anoscopes are conical-tipped cylindrical devices that are inserted into rectum through the anus by the help of the conical tip that enlarges the anal canal and are advanced in rectum up to a particular distance. The handle, a part of the anoscope that remains outside the body, is used to rotate the anoscope 360 degrees inside the rectum.

In the state of the art, some anoscopes have a cavity in their handles into which a light source can be inserted. Thus, the inner part of the anoscope becomes more visible. Such an anoscope has been the subject of the European patent application numbered EP1183991.

Anoscopes with adequately large hole diameters through which devices for surgical interventions can be inserted have been subjects of the above-mentioned European patent application EP1183991; the USA patent applications US20060036129 and US20030130559; and the Japanese patent application JP2003235799.

Although the hole diameter of the anoscope mentioned in the International patent application WO2004064624 is small, it is possible to ligate vessels of the hemorrhoids through a window which is placed near the tip of the anoscope.

In the state of the art, some anoscopes have constant hollow diameters like that mentioned in the U.S. Pat. No. 6,142,933. Upper part of some of these anoscopes is totally open, while some anoscopes, like that mentioned in the USA patent application US20060009797, have wide longitudinal slots. Hemorrhoids that fill these slots can be removed surgically.

Anoscope-resembling cylindrical anal retractors mentioned in the U.S. Pat. No. 5,681,265 have variable inner hollow diameter, however a light source can not be inserted into their handles. Furthermore, performing the procedure of stapled hemorrhoidopexy is not possible using these retractors. The anoscope mentioned in the U.S. Pat. No. 6,142,933 has a constant hole diameter and an open top, and has been planned for the application of a purse string suture to rectum. However, hemorrhoids hanging down from this open top block the vision thereby making it difficult to put a purse string suture to rectum.

For the present applications of the technique, surgical interventions cannot be performed using anoscopes with small inner diameters. Although suturing is possible through the window placed at the tip of the anoscope mentioned in the International patent application WO2004064624, this anoscope can not be used for surgical removal of hemorrhoids, for putting purse string suture to rectum and for stapled hemorrhoidopexy.

None of the anoscopes in the present state of the art are suitable for insertion of a laparoscope and none of them have an adjustable sliding lid that covers the open top of the anoscope. Besides, the above-mentioned anoscopes cannot be used for controlling staple line and they do not allow surgical interventions as necessary.

BRIEF DESCRIPTION OF THE INVENTION

One objective of this invention is to build an anoscope that has an adjustable opening with a sliding lid through which a purse string suture can be applied to the rectal mucosa; that can hold a laparoscope in its handle; and that allows performing stapled hemorrhoidopexy.

Another objective of this invention is to build an anoscope that prevents hanging of hemorrhoids down by an adjustable sliding lid so that the hemorrhoids do not block the vision and they do not complicate application of a purse string suture.

Another objective of this invention is to build an anoscope that has a scale on it allowing measurement of the distance to intervene surgically in the rectum.

Another objective of this invention is to build an anoscope that allows insertion of laparoscope in its handle to visualize and take records of the scene.

Another objective of this invention is to build an anoscope that is sterile and disposable, and thus hygienic.

Another objective of this invention is to build an anoscope that allows control of the staple line and surgical intervention as necessary.

Another objective of this invention is to build an anoscope that has multiple pieces that can readily be assembled or disassociated.

A further objective of this invention is to build an anoscope that allows surgical removal of hemorrhoids using the classical method when its sliding lid is disassociated.

BRIEF DESCRIPTION OF THE DRAWINGS

The anoscope built to achieve the objectives of this invention has been shown in attached figures, where.

Figure 1:
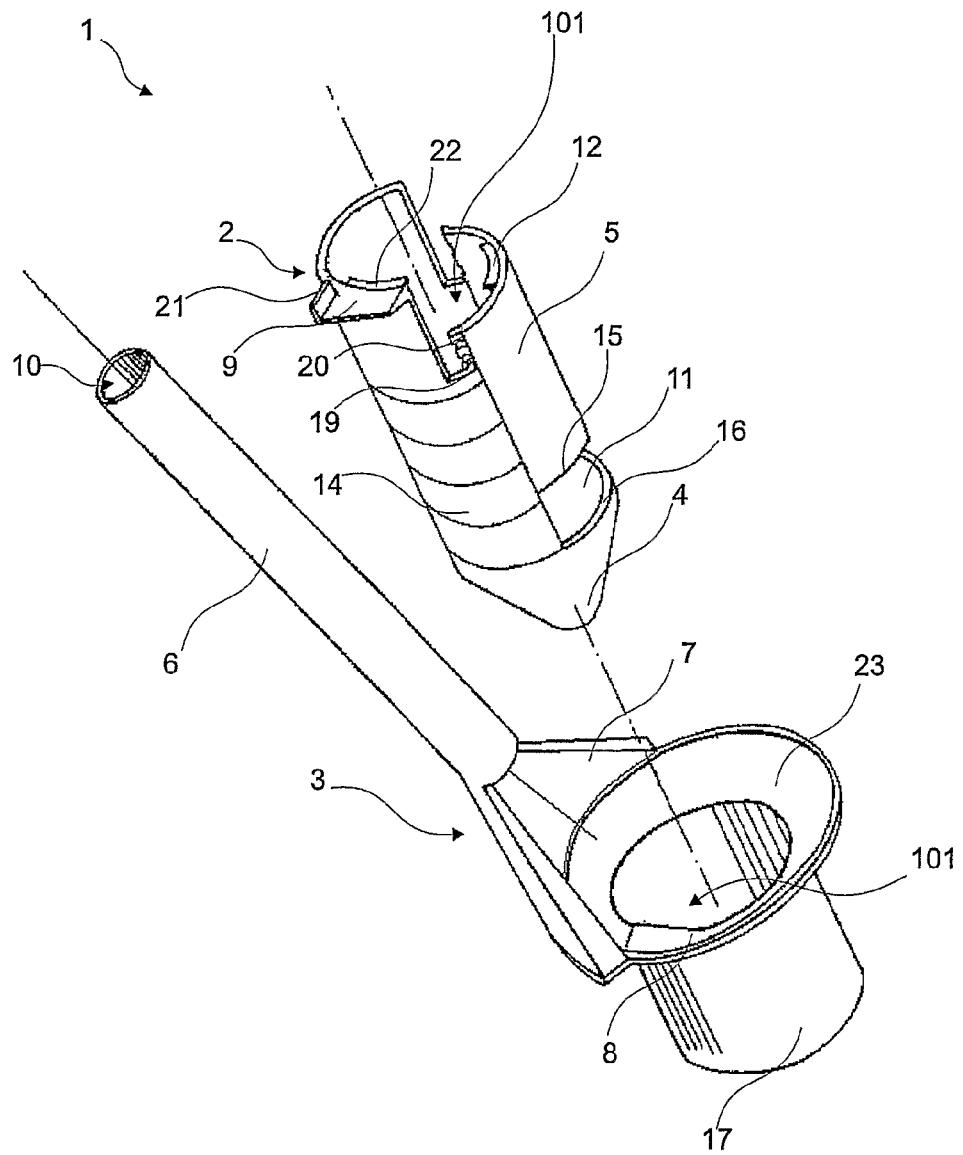
FIG. 1 shows front and back pieces of the anoscope separately.

Each piece in the figures has been numbered as follows:
1. Anoscope
2. Front piece
3. Back piece
4. Nozzle
5. Lid
6. Handle
7. Broadly piece
8. Socket
9. Tongue
10., 101. Cavity
11. Window
12. Protrusion
13. Connection element
14. Body
15. Front border
16. Front tip
17. Extension
18. Cap
19. Slide line of the front piece
20. Slide line of the lid
21. Pillar
22. Console
23. Atrium 24. Handhold
25. Shutter Detailed Description of the Invention The inventive anoscope (1) comprises, in its most basic form, a handle (6), a broadly piece (7), an atrium (23) inside the broadly piece (7), a socket (8), a cylindric extension (17), a back piece (3) that holds a handle (6) with adequate cavity (10) that allows passage of such additional devices as laparoscope; a striped body (14), a nozzle (4), a sliding lid (5), a superficial protrusion (12) inside the lid (5), and a front piece (2) that has a tongue (9) where it meets the back piece (3).

Figure 2:
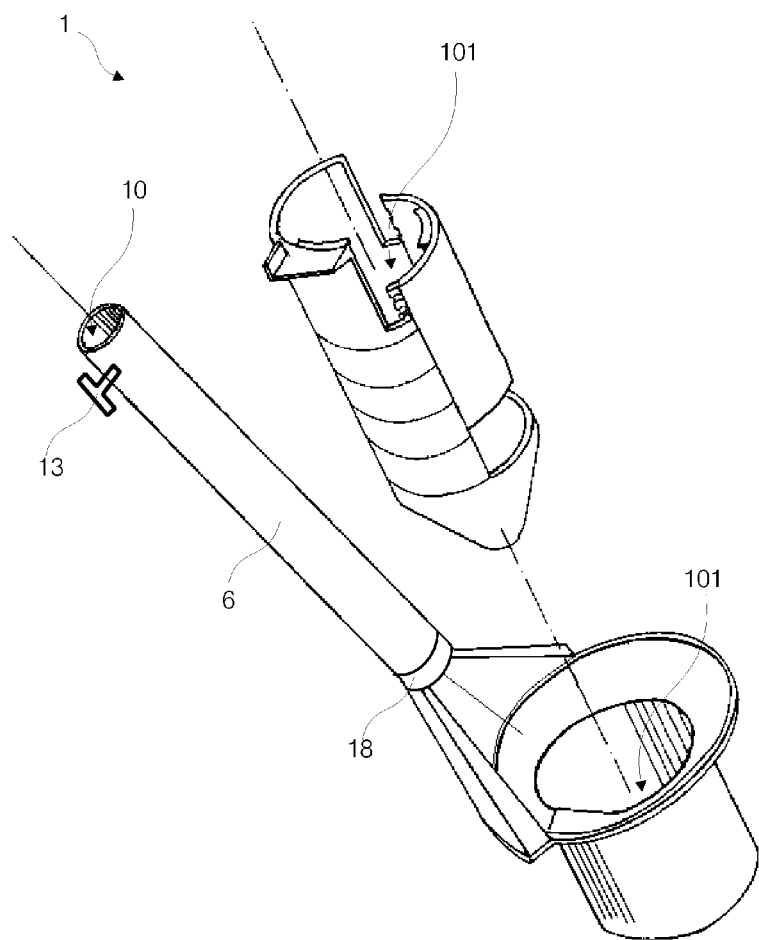
FIG. 2 shows front and back pieces separately in another embodiment thereof.
Figure 6:
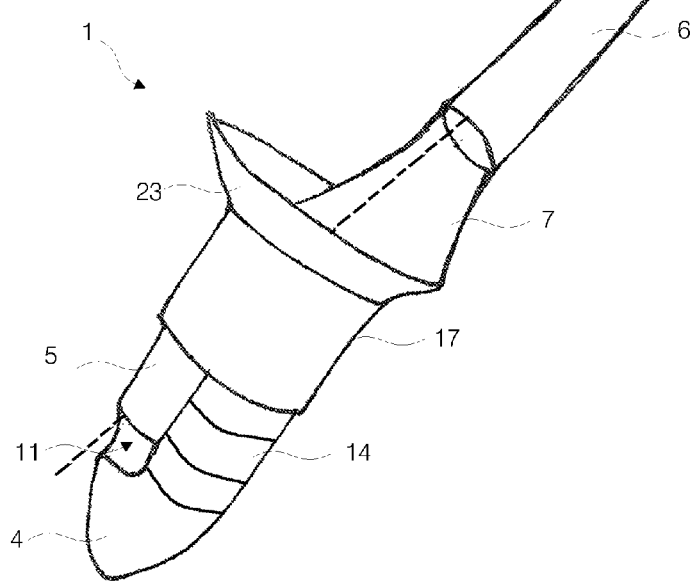
FIG. 6 shows the sliding lid half open in a side schematic view thereof.
Figure 7:
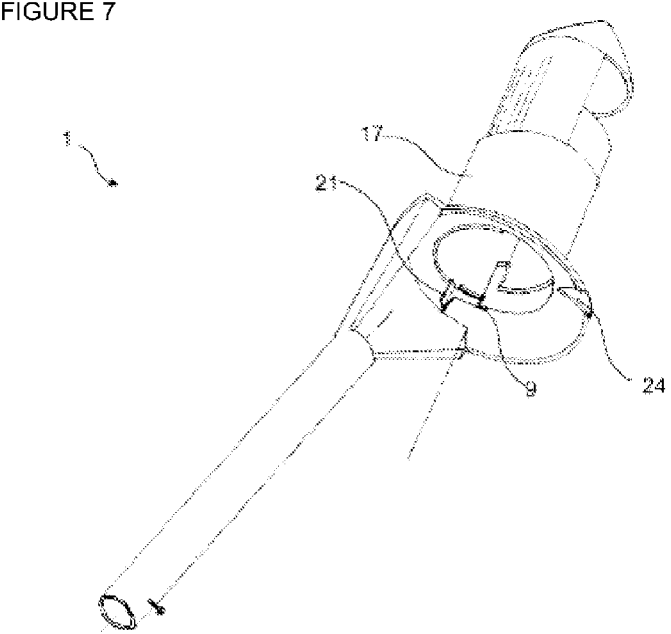
FIG. 7 is a full view thereof.
Figure 8:
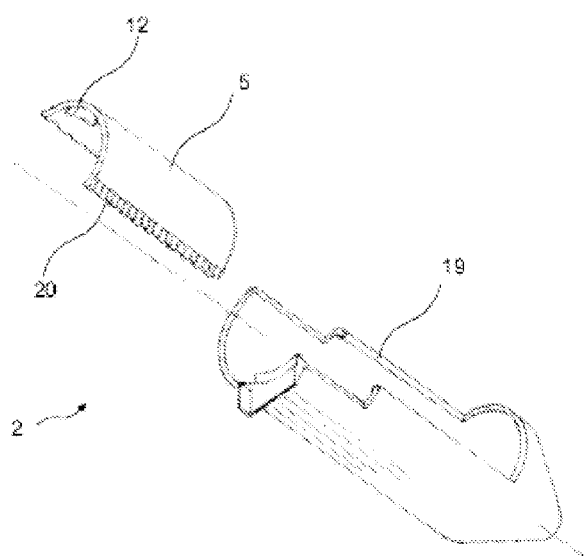
FIG. 8 shows the front piece separated from the lid thereof.

The inventive anoscope (1) has a front piece (2) with a conical-shaped nozzle (4) that narrows at the tip. A sliding lid (5) is placed on the top of the front piece (2). When the sliding lid (5) is closed, upper part of the front piece (2) is completely shut because the front tip (16) of the sliding lid (5) becomes adjacent to the front border (15) of the front piece (2) (FIG. 6). The lid (5) can be opened to the extent required for the type of surgery or it can completely be separated from the front piece (2) (FIGS. 1,2). The lid (5), concordant with the structure of the front piece (2), is protuberant and slide line of the lid (20) ensures movement of the lid (5) on the front piece (2). An interlaced relation between the edges of the front piece (2) and the lid (5) at the slide lines (19,20) ensures that the lid (5) does not fall out of, or into the anoscope (1) (FIGS. 1,2). In one embodiment of the invention, a protruding appearance (19) occurs on the front piece (2) when the dent is on (20) the lid (5). In another embodiment of the invention, a protruding appearance (20) occurs on the lid (5) when the dent (19) is on the front piece (2). Thus, the lid (5) and the front piece (2) have a complete harmony and they move by sliding of one on the other. A protrusion (12) exists at the inner side of the sliding lid (5) that facilitates handling of the lid and its movements (5) (FIGS. 1,2,7). The protrusion (12) is preferably placed at the inner surface of the protuberant part close to the broadly piece (7).

The back piece (3) of the anoscope (1) is comprised of a terminal tube-shaped handle (6) and a broadly piece (7) that combines with the front piece (2) in the middle. There is a cavity (10) inside the handle (6). The handle (6) terminates where it meets the broadly piece (7) without, or with, a small change in its diameter. The broadly piece (7) that starts at the same point with the wide part of the handle (6), opens as a triangle and combines with the atrium (23). The atrium (23) is a flat, concave structure that resembles a hollow plate. A cylindrical extension (17) lies at the same level as the circle formed by the atrium (23) through the front piece (2) surrounding it completely. The broadly piece (7) sits on the front piece (2) like a scoop punctured in the middle. Inner parts of the front piece (2) and the broadly piece (7) of the back piece (3) that combines with the front piece (2) have cavities (101) resembling that of the handle (6). However, the front piece's (2) cavity (101) ends with the nozzle (4). The nozzle (4), located at the beginning (front end) of the front piece (2), is the closed conical tip that facilitates anoscope's (1) insertion through the anal canal.

A socket (8) is placed on the surface of the atrium (23) inside the broadly piece (7). A tongue (9) to be placed into the socket exists between the front (2) and the back (3) pieces. Combination of the front (2) and the back (3) pieces that are otherwise separate is ensured by the transfer of the front piece (2) through the broadly piece (7). After the front piece (2) is transferred through the broadly piece (7) and the extension (17), assembly or disassembly of the atrium and tongue (9) is maintained by rotating the front (2) or the back (3) piece. Thus, the anoscope (1) can be used as a whole or as two separate pieces.

The tongue (9) has both a console (22) coupled to the cavity (101) inside the front piece (2) and a tiny pillar (21) that makes a 90-degree angle with its own axis. The pillar and the console (21, 22) are auxiliary parts that help to rotate or take out the front piece (2).

In another embodiment of the invention, handholds (24) are found in the inner surface of the atrium (23). The socket (8) terminates with the handhold (24).

In another embodiment of the invention, handhold (24) can be placed at the lateral part of the outer circumference of the atrium (23).

Anoscope (1) is a transparent device which can be illuminated. These properties ensure a better inspection of hemorrhoids. Anoscope (1) can be rotated 360 degrees which makes surgical intervention possible in all quadrants of the rectum. The front piece of the anoscope (1) can be taken out by rotating the socket (8) on the broadly piece (7) of the back piece (3) after pushing the pillar (21) on the tongue (9) which is distal (back end) to the front piece (2) (FIG.1). The front (2) and the back (3) pieces are disassociated from each other by pulling the tongue (9) which is taken out of the socket (8) off the console (22) that faces the cavity (101). The cylindric extension (17), a part of the back piece (3), stays in the anal canal after the front piece (2) is taken out. Inner diameter of the extension (17) is large enough to allow passage of any given stapler anvil. Stapler is inserted through the cavity (101) that is inside the back piece (3) but also close to the front piece (2); then it is attached to the anvil that is already placed in the rectum and locked. Rectal mucosa is peeled and stapled in a circular way by pulling the trigger of the stapler. After the stapler is taken out, the front piece (2) is inserted through the cavity (101) into the back piece (3) and the tongue (9) distal to the front piece (2) is inserted into the socket (8) on the broadly piece (7) of the back piece (3) and locked. The lid (5) on the front piece (2) then can be opened to visualize the stapled mucosa line. This window (11) also allows suturing in case of a hemorrhage.

Anoscope (1) is a transparent device which can be illuminated. These properties ensure a better inspection of hemorrhoids. Anoscope (1) can be rotated 360 degrees which makes surgical intervention possible in all quadrants of the rectum. The front piece of the anoscope (1) can be taken out by rotating the socket (8) on the broadly piece (7) of the back piece (3) after pushing the pillar (21) on the tongue (9) which is distal to the front piece (2) (FIG. 1). The front (2) and the back (3) pieces are disassociated from each other by pulling the tongue (9) which is taken out of the socket (8) off the console (22) that faces the cavity (101). The cylindric extension (17), a part of the back piece (3), stays in the anal canal after the front piece (2) is taken out. Inner diameter of the extension (17) is large enough to allow passage of any given stapler anvil. Stapler is inserted through the cavity (101) that is inside the back piece (3) but also close to the front piece (2); then it is attached to the anvil that is already placed in the rectum and locked. Rectal mucosa is peeled and stapled in a circular way by pulling the trigger of the stapler. After the stapler is taken out, the front piece (2) is inserted through the cavity (101) into the back piece (3) and the tongue (9) distal to the front piece (2) is inserted into the socket (8) on the broadly piece (7) of the back piece (3) and locked. The lid (5) on the front piece (2) then can be opened to visualize the stapled mucosa line. This window (11) also allows suturing in case of a hemorrhage.

In order to surgically remove internal hemorrhoids in classical hemorrhoid operations, the sliding lid (5) is pulled until the window (11) is completely opened when the anoscope (1) is inside the rectum. This makes it possible to remove the hemorrhoids that fill the window opening and to put sutures in the surgical area. Classical hemorrhoidal operation is completed after the other two hemorrhoids are removed by rotating the anoscope (1).

A lamp pen or a laparoscope can be placed in the handle (6) of the anoscope (1) since there is enough room in the cavity (10). Longitudinal axis of the handle (6) faces the sliding lid (5) on the front piece (2) of the anoscope (1). Thus, the lamp pen that is placed in the handle illuminates the whole interior of the anoscope (1), in particular, the window (11) opening. Likewise, it is possible to videotape the scene in the window (11) and to videotape the surgical intervention by placing a laparoscope in the handle (6) cavity (10).

While the back piece (3) of the anoscope (1) is still in rectum, the tongue (9) that is distal to the front piece (2) can be unlocked and removed from the socket (8) on the atrium (23) that is located inside the broadly piece (7) of the back piece (3) by pushing the pillar (21), thus allowing free rotation for 360 degrees of the front piece (2) inside the back piece (3) which gives the surgeon a free movement ability.

Figure 3:
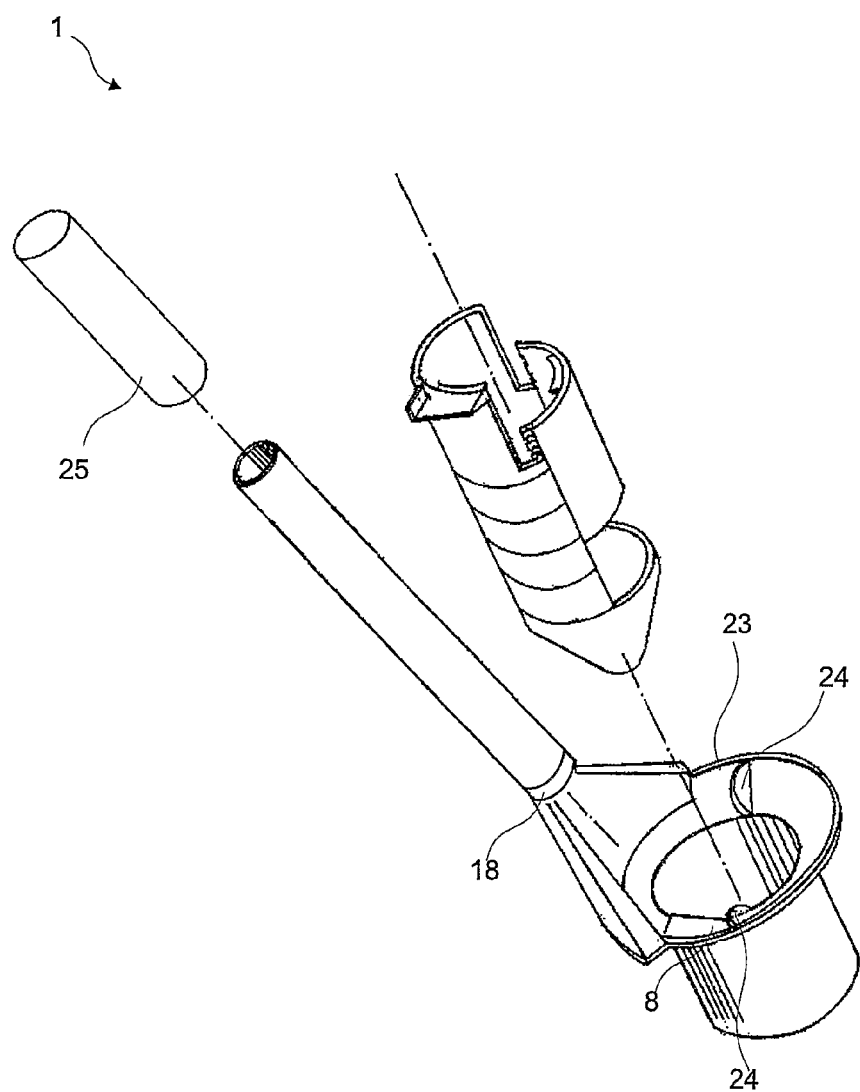
FIG. 3 shows front and back pieces separately in another embodiment thereof.
Figure 4:
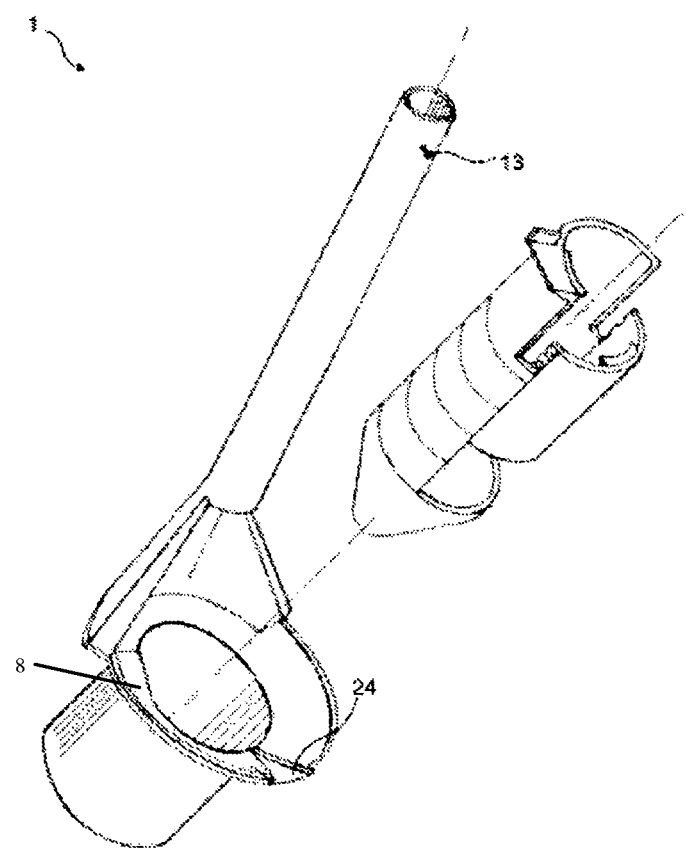
FIG. 4 shows front and back pieces separately in another embodiment thereof.
Figure 5:
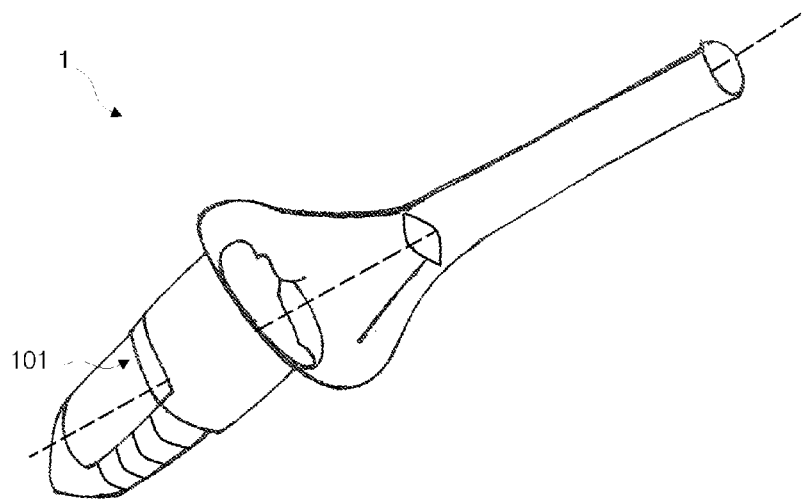
FIG. 5 shows the sliding lid fully open in a top schematic view thereof.

In another embodiment of the invention, a transparent cap (18) that is twisted to open is found on the tip of the handle (6) close to the broadly piece (7) and the front piece (2). The cap (18) must be in closed position if a device like lamp pen will be placed in the handle (6). Devices like lamp pen can be isolated by placing a shutter (25) on the back of the handle (6) (FIG. 3). Thus, a sterile surgery is assured. If a laparoscope will be placed in the handle (6), the cap (18) is opened or totally removed and laparoscope is advanced through the cavity (10) in the handle (6) to the desired distance. Laparoscope's stability is ensured by the connection element (13) that is located on the tip of the handle (6) distal to the anoscope (1) when it reaches the desired distance.

Industrial Applicability

The subject of the invention, anoscope (1), when its sliding lid (5) is closed, can readily be inserted into rectum by the use of its handle (6). It is possible to illuminate the anoscope's (1) interior by placing a laparoscope in its handle (6) which also makes it possible to visualize the operation with other surgeons by transferring the view to a monitor and to videotape it for further use in medical education. The opening ability of the anoscope's (1) sliding lid (5) to the desired extent allows many procedures to be performed. Certain amount of rectal mucosa that does not block the view and peripheral suturing is allowed to enter through the window (11) that is created by opening of the lid (5) for a few milimeters and peripheral suturing is completed by rotating the anoscope (1) for 360 degrees. When the front piece (2) of the anoscope (1) is removed, the handled-part of the anoscope (1) is left behind in the anal canal. This part allows the transfer of stapler anvil and the handle of the anvil is fixated by the tails of the purse string suture. Stapler is passed through the same space and is attached to the anvil. When stapler is fired a mucosal ring is cut and mucosa is stapled circularly thus completing the process. Staple line that formed following hemorrhoidopexy can be checked by opening the sliding lid (5) to the required extent; this makes it possible to surgically intervene in the staple line as necessary.

In another embodiment of the invention, the sliding lid (5) is removed so that the top of the anoscope (1) is fully open to allow the surgeon remove the hemorrhoids that fill the window (11) and then suture the wound in a classical hemorrhoid surgery session. Subsequently, the anoscope (1) is rotated to remove the other two hemorrhoids and complete the surgery session by suturing the relevant wounds.

The invention can be produced as a disposable anoscope (1) which is discarded after single use. Thus, the invention has hygienic property.

Multiple-use applications of the invention is produced from a material that is strong as steel.

Surrounding this basic concept, it is possible to create many different embodiments of the subject of the invention, anoscope (1). The invention principally is reflected by the claims, and cannot be limited to the examples herein.

The invention claimed is:

1. A transparent, illuminateable, multi-piece anoscope (1) comprising:

A back piece (3) and a front piece (2), said back piece (3) containing a terminal tube-shaped handle (6), a broadly piece (7), an atrium (23) and a cylindrical extension (17), said terminal tube-shaped handle (6) comprises a proximal end and distal end and a canal-shaped cavity (10) extending through said handle along a first longitudinal axis between said proximal and distal ends of said handle; said broadly piece (7) opens like a triangle scoop and is attached to said distal end of said handle and is aligned with said handle, Said atrium (23) comprises a flat and concave surface that resembles a hollow plate forming a circle that is attached to the widest edge of said broadly piece (7), said cylindrical extension (17) lies at the same level as the circle formed by the atrium (23) on the back piece (3) and extends along a second longitudinal axis and is configured to reside in the anal canal and allows anvil placement therethrough, and a socket (8) placed on said surface of the atrium (23) inside said broadly piece;

said front piece (2) is coaxially received into said cylindrical extension of said back piece and extends along said second longitudinal axis between an open proximal end and an opposing closed conical distal tip, said front piece further comprises a slide line (19) extending parallel to said second longitudinal axis, wherein said front piece can be locked with said back piece when being coaxially received into said cylindrical extension of said back piece (3), and that allows purse-string suturing by 360 degrees of radial rotation along with the back piece (3) inside the anal canal when locked, and allows rotation inside the back piece (3) when unlocked, A sliding lid (5) having a slide line (20) located on opposing side edges of the lid and extends in a direction parallel to said second longitudinal axis and configured to slide along said slide line (19) of said front piece, so that upon sliding said lid (5) in an axial direction along said slide line of said front piece, a window (11) in the front piece is defined, said sliding lid (5) further comprises a protrusion (12) extending in a transverse direction to said second longitudinal axis at an inner side of the lid (5) that can be grasped to allow the lid's axial translation for opening and closing said window and to enable its complete disassociation from the front piece (2), Said front piece has scale lines on an outer surface that allows measuring the distance that the anoscope enters into the rectum and the degree of the lid (5) axial translation, said first longitudinal axis of said handle faces the front piece and is at an angle relative to said second longitudinal axis of said front piece and said cylindrical extension of said back piece which allows illumination and visualization of the surgical area through the window (11) space, enabling the operation to be recorded by the help of a laparoscope being placed inside said cavity (10);

said front piece further comprises a conical nozzle (4) having round geometry ending with the closed conical tip of the front piece (2) and is located at the front of the front piece (2) configured to prevent irritation of the surgical area by facilitating the entrance of the anoscope in the anal canal;

A tongue (9) extending radially outwardly from said front piece that enables the front piece (2) to be locked inside said cylindrical extension of said back piece (3) by inserting the tongue into the socket, A pillar (21) and a console (22) located on both sides of said tongue (9) that allow rotation of the front piece inside said cylindrical extension of said back piece.

2. The anoscope (1) according to claim 1, further comprising a handhold (24) located on the surface of the atrium (23) that allows rotation of the back piece (3) inside anal canal.

3. The anoscope (1) according to claim 1, further comprising a shutter (25) placed inside the cavity (10) to shut down the proximal end of the handle (6) so as to enable isolation of a laparoscope or similar imaging and illumination devices.

4. The anoscope (1) according to claim 1, further comprising a connection element (13) located on the handle (6) that enables attachment of a laparoscope or similar imaging and illumination devices to be placed inside the cavity (10) of the handle (6).

5. The anoscope (1) according to claim 1, further comprising a transparent cap (18) located at said distal end of the handle (6) adjacent the broadly piece (7) that can be twisted between an open position or closed position following placement of a pen torch or laparoscope inside the cavity of the handle (6).

6. The anoscope (1) according to claim 2, further comprising a shutter (25) placed inside the cavity (10) to shut down the proximal end of the handle (6) so as to enable isolation of a laparoscope or similar imaging and illumination devices.

7. The anoscope (1) according to claim 6, further comprising a connection element (13) located on the handle (6) that enables attachment of a laparoscope or similar imaging and illumination devices to be placed inside the cavity (10) of the handle (6).

8. The anoscope (1) according to claim 7, further comprising a transparent cap (18) located at said distal end of the handle (6) adjacent the broadly piece (7) that can be twisted between an open position or closed position following placement of a pen torch or laparoscope inside the cavity of the handle (6).

* * * * *